(12) United States Patent
Duncan et al.

(10) Patent No.: US 7,388,126 B2
(45) Date of Patent: Jun. 17, 2008

(54) **USE OF NITRIC OXIDE MODULATORS IN *AGROBACTERIUM*-MEDIATED PLANT TRANSFORMATION**

(75) Inventors: David R. Duncan, St. Charles, MO (US); Cristina Ubach, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 225 days.

(21) Appl. No.: 10/905,140

(22) Filed: Dec. 17, 2004

(65) Prior Publication Data

US 2005/0155115 A1 Jul. 14, 2005

Related U.S. Application Data

(60) Provisional application No. 60/481,819, filed on Dec. 19, 2003.

(51) Int. Cl.
*A01H 1/00* (2006.01)
*C12N 15/82* (2006.01)
*C12N 15/87* (2006.01)
*A01N 65/00* (2006.01)
*A61K 36/48* (2006.01)

(52) U.S. Cl. ........................ 800/294; 800/278; 424/757
(58) Field of Classification Search ................ 800/294, 800/278; 424/757; 514/886
See application file for complete search history.

(56) References Cited

U.S. PATENT DOCUMENTS 6,576,780 B1 6/2003 Gapud et al.
6,962,720 B2 * 11/2005 Haridas et al. ............. 424/757

OTHER PUBLICATIONS

Song et al.; Activity of Nitric Oxide Is Dependent On, But Is Partially Required for Function of, Salixylic Acid in the Sgnaling Pathway in Tobacco Systemic Acquired Rsistance; Molecular Plant-Microbe Interactions; vol. 14, No. 12, pp. 1458-1462; 2001.*
Williams, A chemist's view of the nitric oxide story, *Org. Biomol. Chem.* 1:441-449 (2003).

* cited by examiner

*Primary Examiner*—Kent Bell
(74) *Attorney, Agent, or Firm*—Sonnenschein Nath & Rosenthal LLP

(57) ABSTRACT

Use of nitric oxide modulators during the transformation process can enhance *Agrobacterium*-mediated transformation of plants.

10 Claims, 4 Drawing Sheets

USE OF NITRIC OXIDE MODULATORS IN *AGROBACTERIUM*-MEDIATED PLANT TRANSFORMATION

This application claims priority to U.S. Provisional Application 60/481,819, filed Dec. 19, 2003, herein incorporated by reference in its entirety.

BACKGROUND OF INVENTION

This invention relates to plant tissue culture media designed to more efficiently obtain transgenic plant cells from *Agrobacterium*-mediated transformation, and more particularly to plant transformation media containing an effective amount of a nitric oxide modulator.

The ability to transfer genes from a wide range of organisms to crop plants by recombinant DNA technology has become widespread in recent years. This advance has provided enormous opportunities to improve plant resistance to pests, disease and herbicides, and to modify biosynthetic processes to change the quality of plant products. A highly efficient method for transformation of these crop plants continues to be a goal as there is a need for high capacity production of economically important plants.

*Agrobacterium*-mediated transformation is one method for transforming such crop plants and has more recently become more adaptable for use in monocotyledonous plants. Several *Agrobacterium* species mediate the transfer of a specific DNA known as "T-DNA" that can be genetically engineered to carry a desired piece of DNA into the selected plant species. The major events marking the process of T-DNA mediated pathogenesis and ultimately transformation are induction of virulence genes, processing and transfer of the T-DNA to the plant's genome.

Typically, *Agrobacterium*-mediated genetic transformation of plants involves several steps. The first step, in which the *Agrobacterium* and plant cells are brought into contact with each other, is generally called "inoculation." Following the inoculation step, the *Agrobacterium* and plant cells/tissues are usually grown together for a period of several hours to several days or more under conditions suitable for growth and T-DNA transfer. This step is termed "co-culture". Following co-culture and T-DNA delivery, the plant cells are often treated with bactericidal or bacteriostatic agents to prevent further growth of the *Agrobacterium*. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, one or more "selection" steps usually follow it. Both the "delay" and "selection" steps typically include bactericidal or bacteriostatic agents to prevent further growth of any remaining *Agrobacterium* cells because the growth of *Agrobacterium* cells is undesirable after the infection (inoculation and co-culture) process.

Modulation of the plant response to *Agrobacterium* is an important part of *Agrobacterium* transformation, because *Agrobacterium* transformation is a variation of the disease process caused by *Agrobacterium*. One of the variables is getting the right amount of infection to cause efficient transformation without too much infection overwhelming the plant and doing damage.

In plants, nitric oxide (NO) has been implicated in disease resistance and various types of defense responses to environmental stresses (Leshem et al., Plant Physiology Biochemistry 35: 573-579, 1997; Plant Physiology and Biochemistry 36: 825-833, 1998; Millar and Day, Trends in Plant Science 2: 289-290, 1997; Klessig, Proceedings National Academy of Sciences USA 97: 8849-8855, 1999; Magalhaes et al., Physiology Molecular Biology Plants 5: 115-125, 1999; Pedroso et al., Plant Science 157: 173-180, 2000; Pedroso et al., Journal of Experimental Botany 51: 1027-1036, 2000; Garces et al., Annals of Botany 87: 567-574, 2001). In animals, NO is produced from L-arginine by both constitutive and inducible NO-synthases (NOS) (Garvin, In: Sitaramayya A. ed., Introduction to Cellular Signal Transduction. Boston. pp 177-212, 1999). A similar pathway may exist in plants because NO production inhibitors used with animal cells also inhibit NO production in plants (Guo et al., Science 302: 100-103, 2003). NO can also be generated in plants as a by-product of nitrate reductase, nitrogen fixation, or respiration (Klepper, Plant Physiology 93: 26-32, 1990; Norditake et al., Plant Cell and Physiology).

Because NO has been implicated in defense responses, its control or elimination may increase pathogen infection such as that of *Agrobacterium* during plant transformation. The present invention provides a novel method of increasing *Agrobacterium*-mediated transformation through the use of compounds and processes that modulate endogenous NO levels.

SUMMARY OF INVENTION

A method for genetically transforming a plant cell, tissue, or other suitable explant and regenerating a transformed plant therefrom is provided. In accordance with the present invention, the method provides for introducing a nucleic acid into the genome of a plant cell wherein an effective amount of a nitric oxide modulator is included in the transformation medium. In the practice of the method, the plant cell, tissue or explant is placed in contact with a transformation media comprising an amount of at least one nitric oxide modulator sufficient to enhance the efficiency of transformation of the plant cell, tissue, or explant during the transformation process as compared to a plant cell, tissue, or explant being transformed in the absence of a nitric oxide modulator.

The invention further provides plant transformation media compositions comprising an effective amount of at least one nitric oxide modulator. The media may be liquid, solid, or semi-solid, and the at least one nitric oxide modulator may be included in any of the particular media used during the transformation process, e.g., the pre-inoculation, inoculation, co-cultivation, delay, selection, shoot induction, elongation, regeneration or rooting media.

Also provided is a method of improving the efficiency of transformation of a plant cell, tissue or explant in the presence of at least one nitric oxide modulator, wherein the at least one nitric oxide modulator is included in the plant transformation media in which the plant cell, tissue, or explant is cultured during the transformation process.

More specifically, the invention also provides a method for transforming dicotyledonous and monocotyledonous plant tissue and regenerating fertile transgenic plants therefrom comprising the inclusion of an effective amount of at least one nitric oxide modulator in at least one of the plant transformation media during the transformation process.

Also provided is a method of treating a plant cell during an *Agrobacterium* transformation process with at least one nitric oxide modulator. Transformed plants produced by the method of the present invention are also provided.

DETAILED DESCRIPTION

Figure 1:
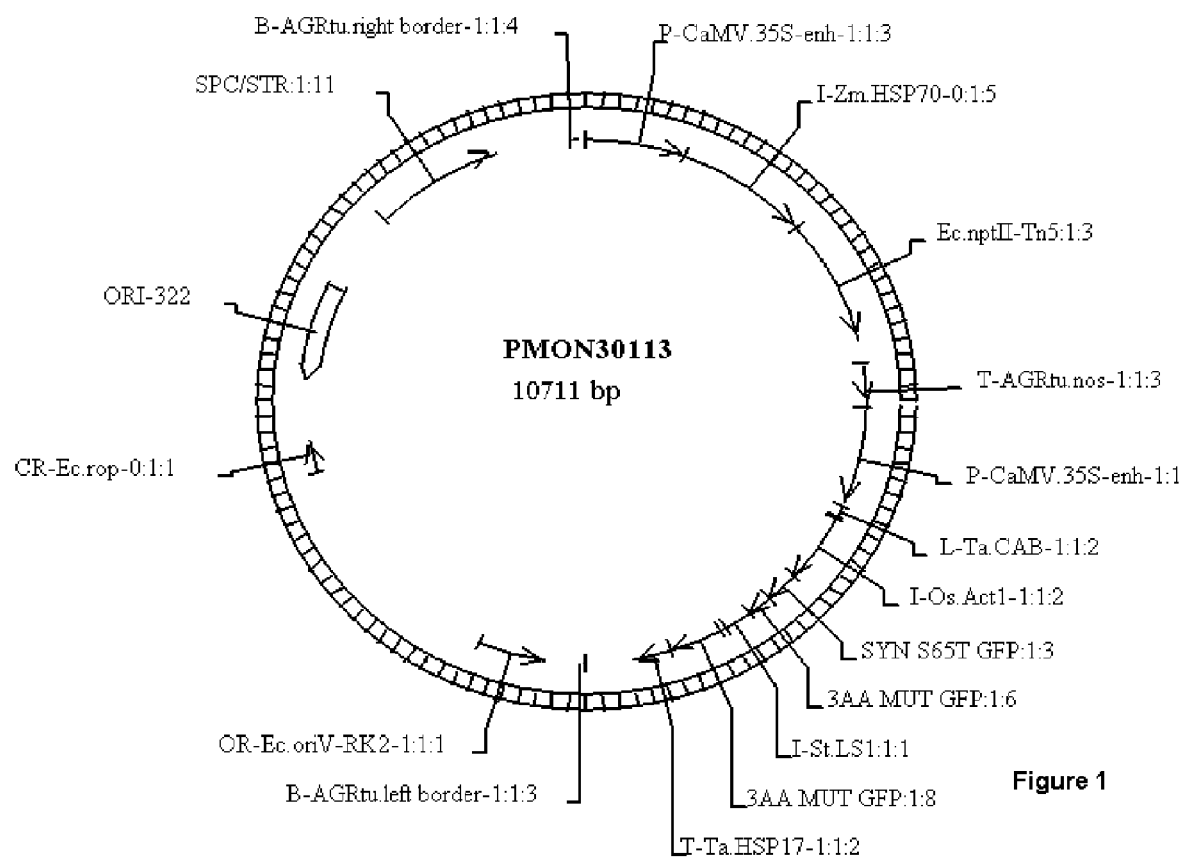
FIG. 1 is a schematic map of plasmid pMON30113.

It has been discovered that the inclusion of at least one modulator of nitric oxide in at least one plant transformation medium during the *Agrobacterium* transformation process increases the efficiency of transformation of a plant explant with a selected nucleic acid fragment.

A "nitric oxide modulator" is a substance or process that alters the normal levels of nitric oxide in the plant cell or tissue. They may be NO donors, which may be directly or indirectly involved in the increase of NO levels, or they may be NO inhibitors, which may be directly or indirectly involved in the decrease of NO levels, or they may be NO scavengers.

"Transformation media" or "plant transformation media" as used herein, refers to the plant tissue culture media, whether liquid, solid, or semi-solid, used during the process of the transformation of plant cells, tissues, parts or other plant tissue explants and subsequent regeneration of whole, transgenic plants therefrom. Depending upon the plant species being transformed and the transformation process being used, the transformation media may include, but is not limited to, the isolation media, induction media, delay media, selection media, or regeneration media.

"Efficiency of transformation or regeneration" or "transformation efficiency," as used herein, refers to the percentage of transgenic events produced per explant or the percentage of transgenic plants produced per explant. The efficiency of transformation may also be described in the number of "escapes" resulting from the transformation process.

An "event," as used herein, refers to a particular genomic insertion of the desired gene into a specific plant.

An "escape," as used herein, refers to a plant that survives the selection process without having the gene encoding for resistance to the selectable marker stably integrated into the plant genome.

In a preferred embodiment of the invention and as further detailed in the Examples below, nitric oxide modulators have been added to plant transformation media to improve the efficiency of *Agrobacterium*-mediated transformation.

Without intending the invention to be bound by this mechanism, NO may play a role in the induction of cell development in plants because it has been observed that NO inhibitors decreased the callus response in corn embryos. Controlling NO production and balancing the levels for transformation and callus production has been found to enhance transformation efficiency. Manipulation of NO levels in transformation also find utility in transformation systems that do not involve a callus step, such as meristem transformation in soybean.

Nitric oxide (NO) donors include any compound or process that directly or indirectly causes the increase of NO levels. Such compounds or processes include, but are not limited to, sodium nitroprusside (SNP), (±)—S-nitroso-N-acetylpenicillamine (SNAP); S-nitrosocaptopril (CapNO; S—NO-Cap); S-nitrosoglutathione (GSNO; SNOG); S-nitrosoglutathione monoethyl ester (GSNO-MEE; SNOG-MEE); NOC-5 (3-aminopropyl)-1-hydroxy-3-isopropyl-2-oxo-1-triazene); NOC-7 (1-hydroxy-3-methyl-3-(methylaminopropyl)-2-oxo-1-triazene); NOC-9 (6-(2-hydroxyl-1-methyl-2-nitrosohydrazino)-N-methyl-1-hexanamine); NOC-12 (3-ethyl-3-(ethylaminoethyl)-1-hydroxy-2-oxo-1-triazene); and NOC-18 (3,3-bis-(aminoethyl)-1-hydroxy-2-oxo-1-triazene).

NO inhibitors include any compound or process that directly or indirectly causes the decrease of NO levels. Such compounds or processes include, but are not limited to, $N^G$-monomethyl-L-arginine, monoacetate salt ($N^G$—Me-L-Arg, AcOH; L-NMMA); $N^G$-monomethyl-L-homoarginine, monoacetate salt (NMMHA, AcOH); $N^G$-monoethyl-L-arginine, monoacetate salt (NMEA, AcOH); $N^G$-monomethyl-L-arginine, di-p-hydroxyazobenzene-p'-sulfonate salt ($N^G$-Me-L-Arg,diHABS; L-NMMA); and cytokinins. NO scavengers such as 2-(4-Carboxyphenyl)-4,4,5,5-tetramethylimidazoline-1-oxyl-3-oxide.potassium salt (Carboxy-PTIO) may also be used. Other nitric oxide synthase inhibitors are described in U.S. Pat. No. 6,576,780, WO 96/35677, WO 96/33175, WO 96/15120, WO 95/11014, WO 95/11231 WO 95/25717, WO 95/24382, WO 94/12165, WO 94/14780, WO 93/13055, EP 0446699A1 and U.S. Pat. No. 5,132,453, the disclosures of which are hereby incorporated by reference in their entirety as if written herein. Inhibitory processes include clinorotation in which the plant cells or tissues are on a platform at about a 45-degree angle and rotated at about 10 rpm.

The amount of nitric oxide modulator to include in the plant transformation media and in which media during the transformation/regeneration process it should be included to be most efficacious varies from plant species to plant species and the transformation system being employed. It is anticipated that an effective amount of a nitric oxide modulator would be from about 1 µM to about 10 mM. As described herein, the inclusion of nitric oxide modulators in plant transformation media may advantageously be used with any plant species. Particularly preferred species for practice of the present invention include tomato, cotton, potato, wheat, corn, rice, and oilseeds, such as soybean, sunflower, and oilseed rape species.

It may also be desirable to use combinations of NO modulators in the same transformation process. For example, first a nitric oxide inhibitor may be used to facilitate the transformation process. Then, a nitric oxide donor may be used to enhance plant cell growth.

The present invention provides for obtaining a fertile transgenic plant and a method for the transformation of plant cells or tissues and regeneration of the transformed cells or tissues into a fertile, differentiated transformed plant. Although various transformation systems are well known to those skilled in the art, a brief description of the process is provided below.

Typically, to initiate a transformation process in accordance with the present invention, it is first necessary to select the genetic components desired to be inserted into the plant cells or tissues. Genetic components may include any nucleic acid that is introduced into a plant cell or tissue using the method according to the invention. Genetic components can include non-plant DNA, plant DNA, or synthetic DNA.

In a preferred embodiment, the genetic components are incorporated into a DNA composition such as a recombinant, double-stranded plasmid or vector molecule comprising at least one of the following types of genetic components: (a) a promoter that functions in plant cells to cause the production of an RNA sequence, (b) a structural DNA sequence that causes the production of an RNA sequence that encodes a desired protein or polypeptide, and (c) a 3' non-translated DNA sequence that functions in plant cells to cause the polyadenylation of the 3' end of the RNA sequence. The vector may also contain a number of genetic components to facilitate transformation of the plant cell or tissue and regulate expression of the desired gene(s).

The genetic components are typically oriented so as to express an mRNA, which in one embodiment can be translated into a protein. The expression of a plant structural coding sequence (a gene, cDNA, synthetic DNA, or other DNA) that exists in double-stranded form involves transcription of messenger RNA (mRNA) from one strand of the DNA by RNA polymerase and subsequent processing of the mRNA primary transcript inside the nucleus. This processing involves a 3' non-translated region that includes polyadenylation of the 3' ends of the mRNA.

Means for preparing plasmids or vectors that contain the desired genetic components and that can be used to transform plants and methods of making those vectors are well known in the art. Vectors typically consist of a number of genetic components, including, but not limited to, regulatory elements such as promoters, leaders, introns, and terminator sequences. Regulatory elements are also referred to as cis- or trans-regulatory elements, depending on the proximity of the element to the sequences or gene(s) they control.

Transcription of DNA into mRNA is regulated by a region of DNA usually referred to as the "promoter." The promoter region contains a sequence of bases that signals RNA polymerase to associate with the DNA and to initiate the transcription into mRNA using one of the DNA strands as a template to make a corresponding complementary strand of RNA.

A number of promoters that are active in plant cells have been described in the literature. Such promoters include, but are not limited to, the nopaline synthase (NOS) and octopine synthase (OCS) promoters, which are carried on tumor-inducing plasmids of *Agrobacterium tumefaciens*; the caulimovirus promoters such as the cauliflower mosaic virus (CaMV) 19S and 35S promoters and the figwort mosaic virus (FMV) 35S promoter; the enhanced CaMV35S promoter (e35S); and the light-inducible promoter from the small subunit of ribulose bisphosphate carboxylase (ss-RUBISCO, a very abundant plant polypeptide). All of these promoters have been used to create various types of DNA constructs that have been expressed in plants. Promoter hybrids can also be constructed to enhance transcriptional activity or to combine desired transcriptional activity, inducibility, and tissue or developmental specificity.

Thus, promoters that function in plants may be inducible, viral, synthetic, constitutive as described, temporally regulated, spatially regulated, and/or spatio-temporally regulated. Other promoters that are tissue-enhanced, tissue-specific, or developmentally regulated are also known in the art and envisioned to have utility in the practice of this invention. Useful promoters may be obtained from a variety of sources such as plants and plant DNA viruses. As described below, it is preferred that the particular promoter selected should be capable of causing sufficient expression to result in the production of an effective amount of the gene product of interest.

The promoters used in the DNA constructs (i.e., chimeric/recombinant plant genes) of the present invention may be modified, if desired, to affect their control characteristics. Promoters can be derived by means of ligation with operator regions, random or controlled mutagenesis, etc. Furthermore, the promoters may be altered to contain multiple "enhancer sequences" to assist in elevating gene expression.

The mRNA produced by a DNA construct of the present invention may also contain a 5' non-translated leader sequence. This sequence can be derived from the promoter selected to express the gene and can be specifically modified so as to increase translation of the mRNA. The 5' non-translated regions can also be obtained from viral RNAs, from suitable eukaryotic genes, or from a synthetic gene sequence. Such "enhancer" sequences may be desirable to increase or alter the translational efficiency of the resultant mRNA. The present invention is not limited to constructs wherein the non-translated region is derived from both the 5' non-translated sequence that accompanies the promoter sequence. Rather, the non-translated leader sequence can be derived from unrelated promoters or genes. Other genetic components that serve to enhance expression or affect transcription or translation of a gene are also envisioned as genetic components. The 3' non-translated region of the chimeric constructs preferably contains a transcriptional terminator, or an element having equivalent function, and a polyadenylation signal, which functions in plants to polyadenylate the 3' end of the RNA. Examples of suitable 3' regions are (1) the 3' transcribed, non-translated regions containing the polyadenylation signal of *Agrobacterium* tumor-inducing (Ti) plasmid genes, such as the nopaline synthase (NOS) gene, and (2) plant genes such as the soybean storage protein genes and the small subunit of the ribulose-1,5-bisphosphate carboxylase (ssRUBISCO) gene. An example of a preferred 3' region is that from the ssRUBISCO E9 gene from pea.

Typically, DNA sequences located a few hundred base pairs downstream of the polyadenylation site serve to terminate transcription. The DNA sequences are referred to herein as transcription-termination regions. The regions are required for efficient polyadenylation of transcribed messenger RNA (mRNA) and are known as 3' non-translated regions. RNA polymerase transcribes a coding DNA sequence through a site where polyadenylation occurs.

In many transformation systems, it is preferable that the transformation vector contains a selectable, screenable, or scorable marker gene. These genetic components are also referred to herein as functional genetic components, as they produce a product that serves a function in the identification of a transformed plant, or a product of desired utility. The DNA that serves as a selection device functions in a regenerable plant tissue to produce a compound that confers upon the plant tissue resistance to an otherwise toxic compound. Genes of interest for use as a selectable, screenable, or scorable marker would include, but are not limited to, β-glucuronidase (GUS), green fluorescent protein (GFP), luciferase (LUX), antibiotics like kanamycin (Dekeyser et al., Plant Physiol., 90: 217-223, 1989), and herbicides like glyphosate (Della-Cioppa et al., Bio/Technology, 5: 579-584, 1987). Other selection devices can also be implemented, including, but not limited to, tolerance to phosphinothricin, bialaphos, and positive selection mechanisms (Joersbo et al., Mol. Breed., 4: 111-117, 1998) and would still fall within the scope of the present invention.

The present invention can be used with any suitable plant transformation plasmid or vector containing a selectable or screenable marker and associated regulatory elements as described, along with one or more nucleic acids (a structural gene of interest) expressed in a manner sufficient to confer a particular desirable trait. Examples of suitable structural genes of interest envisioned by the present invention include, but are not limited to, genes for insect or pest tolerance, genes for herbicide tolerance, genes for quality improvements such as yield, nutritional enhancements, environmental or stress tolerances, or genes for any desirable changes in plant physiology, growth, development, morphology, or plant product(s).

Alternatively, the DNA coding sequences can effect these phenotypes by encoding a non-translatable RNA molecule that causes the targeted inhibition of expression of an endogenous gene, for example via antisense—or cosuppression-mediated mechanisms (see, for example, Bird et al., Biotech Gen. Engin. Rev., 9: 207-227, 1991). The RNA could also be a catalytic RNA molecule (i.e., a ribozyme) engineered to cleave a desired endogenous mRNA product (see for example, Gibson and Shillitoe, Mol. Biotech. 7: 125-137, 1997). More particularly, for a description of anti-sense regulation of gene expression in plant cells see U.S. Pat. No. 5,107,065 and for a description of gene suppression in plants by transcription of a dsRNA see U.S. Pat. No. 6,506,559, U.S. Patent Application Publication No. 2002/0168707 A1, and U.S. patent application Ser. Nos. 09/423,143 (see WO 98/53083), 09/127,735 (see WO 99/53050) and 09/084,942 (see WO 99/61631), all of which are incorporated in their entirety herein by reference. Thus, any gene that produces a protein or mRNA that expresses a phenotype or morphology change of interest is useful for the practice of the present invention.

Exemplary nucleic acids that may be introduced by the methods encompassed by the present invention include, for example, DNA sequences or genes from another species, or even genes or sequences that originate with or are present in the same species but are incorporated into recipient cells by genetic engineering methods rather than classical reproduction or breeding techniques. The term exogenous, however, is also intended to refer to genes that are not normally present in the cell being transformed or to genes that are not present in the form, structure, etc., as found in the transforming DNA segment or to genes that are normally present but a different expression is desirable. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

In light of this disclosure, numerous other possible selectable or screenable marker genes, regulatory elements, and other sequences of interest will be apparent to those of skill in the art. Therefore, the foregoing discussion is intended to be exemplary rather than exhaustive.

After the construction of the plant transformation vector or construct, the nucleic acid molecule, prepared as a DNA composition in vitro, is introduced into a suitable host such as E. coli and mated into another suitable host such as Agrobacterium, or directly transformed into competent Agrobacterium. These techniques are well-known to those of skill in the art and have been described for a number of plant systems including soybean, cotton, and wheat (see, for example, U.S. Pat. Nos. 5,569,834 and 5,159,135 and WO 97/48814, which are herein incorporated by reference in their entirety). Those of skill in the art would recognize the utility of Agrobacterium-mediated transformation methods. Preferred strains include, but are not limited to, Agrobacterium tumefaciens strain C58, a nopaline strain that is used to mediate the transfer of DNA into a plant cell; octopine strains, such as LBA4404; or agropine strains, e.g., EHA101, EHA105, or EHA109. The use of these strains for plant transformation has been reported, and the methods are familiar to those of skill in the art.

The present invention can be used with any transformable cell or tissue. Those of skill in the art recognize that transformable plant tissue generally refers to tissue that can have exogenous DNA inserted in its genome and under appropriate culture conditions can form into a differentiated plant. Such tissue can include, but is not limited to, callus tissue, hypocotyl tissue, cotyledons, meristematic tissue, roots, and leaves. For example, transformable tissues can include calli or embryoids from anthers, microspores, inflorescences, and leaf tissues. Other tissues are also envisioned to have utility in the practice of the present invention, and the desirability of a particular explant for a particular plant species is either known in the art or may be determined by routine screening and testing experiments whereby various explants are used in the transformation process and those that are more successful in producing transgenic plants are identified. In one embodiment of the present invention, corn callus is used as the starting explant material.

Methods for transforming dicots by use of Agrobacterium tumefaciens and obtaining transgenic plants have been published for a number of crops including cotton, soybean, Brassica, and peanut.

Successful transformation of monocotyledonous plants by Agrobacterium-based methods have also been reported. Transformation and plant regeneration have been achieved and reported at least in asparagus, barley, maize, oat, rice, sugarcane, tall fescue, and wheat.

The present invention finds particular use in Agrobacterium-mediated transformation processes. Agrobacterium-inoculated explants are typically cultured on an appropriate co-culture medium to allow for transfer of the genetic component containing the gene of interest to be introduced into the plant cells/tissue for incorporation into its genome. Appropriate co-culture media are typically known for each culture system or can be determined by one of skill in the art. In accordance with the present invention, the co-culture medium may contain an effective amount of at least one NO modulator.

The Agrobacterium-inoculated explants are then typically cultured on an appropriate medium containing an agent to inhibit Agrobacterium growth. This medium is usually referred to as a delay medium or a selection medium, as described below. The Agrobacterium-inoculated explants are cultured on such a medium generally from one to fourteen days, preferably from two to seven days. Those of skill in the art are aware of the appropriate media components to inhibit Agrobacterium growth. Such media components would include, but are not limited to, antibiotics such as carbenicillin or cefotaxime. After the culture step to inhibit Agrobacterium growth, and preferably before the explants can be placed on selective media, they can be analyzed for efficiency of DNA delivery by a transient assay that detects the presence of a gene contained on the transformation vector, including, but not limited to, a screenable marker gene such as the gene that codes for β-glucuronidase (GUS). The total number of blue spots (indicating GUS expression) for a selected number of explants is used as a positive correlation of DNA transfer efficiency.

In a preferred embodiment, after incubation on non-selective medium containing the antibiotics to inhibit Agrobacterium growth without selective agents (delay medium), the explants are cultured on selective growth medium including, but not limited to, a callus-inducing medium containing a selective agent. Typical selective agents have been described and include, but are not limited to, antibiotics such as geneticin (G418), paromomycin, kanamycin, or other chemicals such as glyphosate. Delay media or selection media may also contain an effective amount of at least one NO modulator. The plant tissue cultures surviving the selection medium are subsequently transferred to a regeneration medium suitable for the production of transformed plantlets. Regeneration can be carried out over several steps. Those of skill in the art are aware of the numerous types of media and transfer requirements that can be implemented and optimized for each plant system for plant transformation and regeneration. Consequently, such media and culture conditions disclosed in the present invention can be modified or substituted with nutritionally equivalent components, or similar processes for selection and regeneration, and still fall within the scope of the present invention.

The transformants produced are subsequently analyzed to determine the presence or absence of a particular nucleic acid of interest contained on the transformation vector. Molecular analyses can include, but are not limited to, Southern blots (Southern, Mol. Biol., 98: 503-517, 1975) or PCR (polymerase chain reaction) analyses. These and other well known methods can be performed to confirm the stability of the transformed plants produced by the methods disclosed. These methods are well known to those of skill in the art and have been reported (see, for example, Sambrook et al., *Molecular Cloning: A Laboratory Manual*, Second Edition, Cold Spring Harbor Laboratory Press, Cold Spring Harbor, N.Y., 1989).

The previous discussion is merely a broad outline of standard transformation and regeneration protocols. One of skill in the art knows that specific crops and specific protocols can vary somewhat from the broad outline. A variety of media can be used in each system as well. Those of skill in the art are familiar with the variety of tissue culture media that, when supplemented appropriately, support plant tissue growth and development. These tissue culture media can either be purchased as a commercial preparation or custom prepared and modified by those of skill in the art. Examples of such media include, but are not limited to, Murashige and Skoog (Murashige and Skoog, Physiol. Plant, 15: 473-497, 1962), N6 (Chu et al., Scientia Sinica 18: 659, 1975), Linsmaier and Skoog (Linsmaier and Skoog, Physio. Plant., 18: 100, 1965), Uchimiya and Murashige (Uchimiya and Murashige, Plant Physiol. 15: 473, 1962), Gamborg's media (Gamborg et al., Exp. Cell Res., 50: 151, 1968), D medium (Duncan et al., Planta, 165: 322-332, 1985), McCown's Woody plant media (McCown and Lloyd, HortScience 16: 453, 1981), Nitsch and Nitsch (Nitsch and Nitsch, Science 163: 85-87,1969), and Schenk and Hildebrandt (Schenk and Hildebrandt, Can. J. Bot. 50: 199-204, 1972) or derivations of these media supplemented accordingly. Those of skill in the art are aware that media and media supplements such as nutrients and growth regulators for use in transformation and regeneration are usually optimized for the particular target crop or variety of interest.

EXAMPLES

The following examples further illustrate the present invention. They are in no way to be construed as a limitation in scope and meaning of the claims.

Example 1

Bacterial Strains and Plasmids

Figure 2:
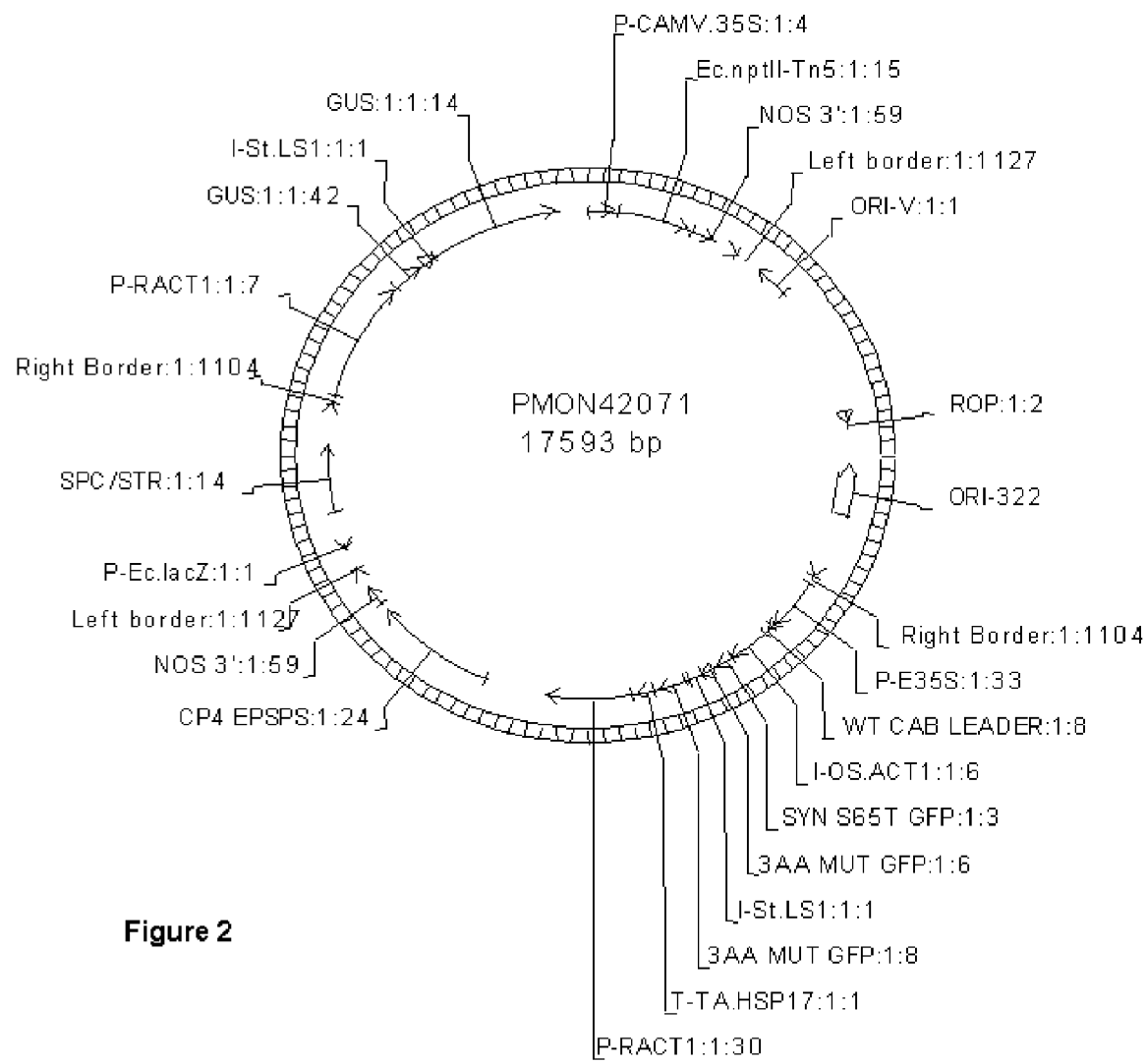
FIG. 2 is a schematic map of plasmid pMON42071.
Figure 3:
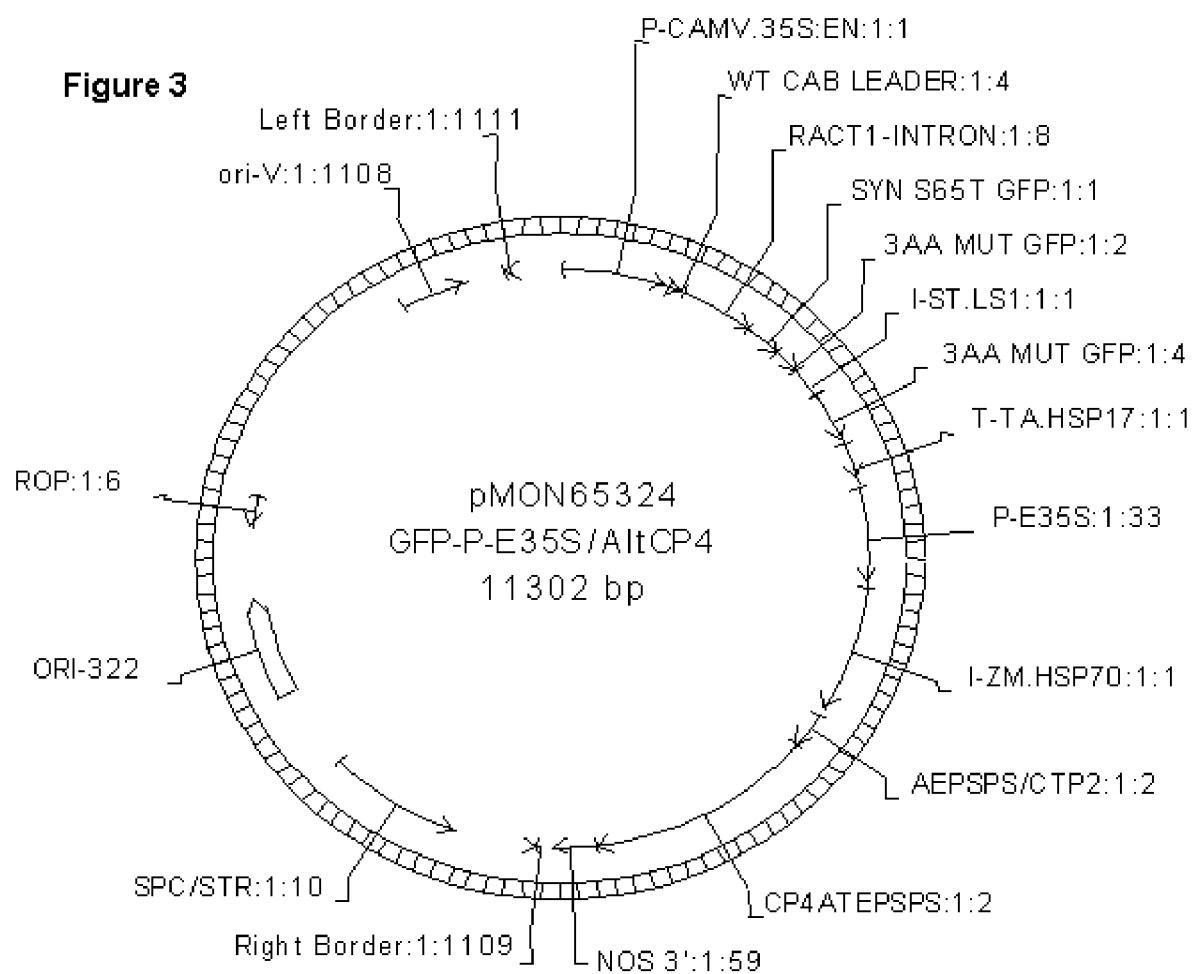
FIG. 3 is a schematic map of plasmid pMON65324.
Figure 4:
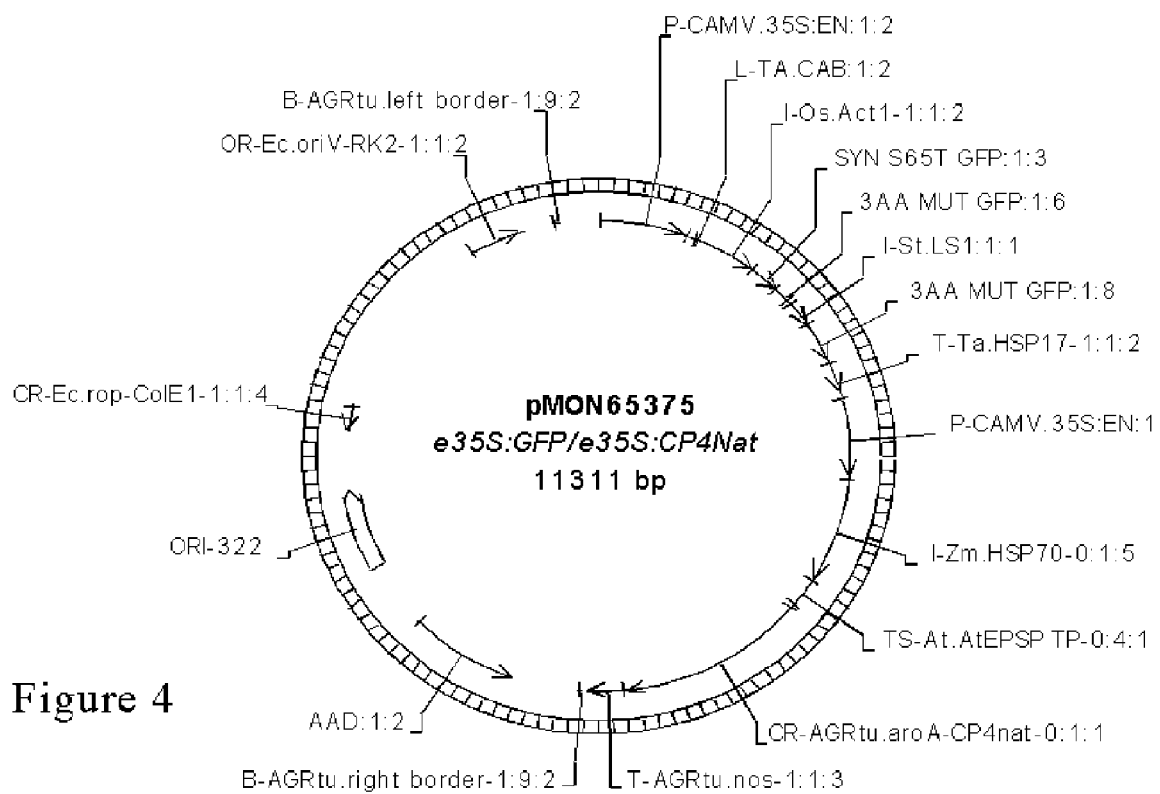
FIG. 4 is a schematic map of plasmid pMON65375.

*Agrobacterium tumefaciens* strain ABI is harbored with the binary vectors pMON30113 (FIG. 1), pMON42071 (FIG. 2), pMON65324 (FIG. 3), or pMON65375 (FIG. 4). The T-DNA in pMON30113 contains a neomycin phosphotransferase II gene (npdII) as the selectable marker and a green fluorescence protein gene (gfp) screenable marker, both driven by an e35S promoter, respectively. pMON42071 has 2 T-DNA, with npdII driven by an e35S promoter and GUS genes by a rice actin promoter on one T-DNA and CP4 driven by a rice actin promoter and gfp genes by an e35S promoter on another. pMON65324 and pMON65375 have CP4 and gfp genes each driven by an e35S promoter also on the T-DNA.

Example 2

Preparation of *Agrobacterium*

*Agrobacterium* ABI containing a vector in glycerol stock is streaked out on solid LB medium supplemented with antibiotics kanamycin (50 mg/L), spectinomycin (50 mg/L), streptomycin (50 mg/L) and chloramphenicol (25 mg/L) and incubated at 28° C. for 2 days. Two days before *Agrobacterium* inoculation of the maize immature embryos, one colony or a small loop of *Agrobacterium* from the *Agrobacterium* plate is picked up and inoculated into 25 mL of liquid LB medium supplemented with 100 mg/L of spectinomycin and 50 mg/L of kanamycin in a 250-mL flask. The flask is placed on a shaker at approximately 150 rpm and 28° C. overnight. The *Agrobacterium* culture is then diluted (1 to 5) in the same liquid medium and put back on the shaker. Several hours later, one day before inoculation, the *Agrobacterium* cells are spun down at 3500 rpm for 15 min. The bacterium cell pellet is re-suspended in induction broth with 200 µM of acetosyringone and 50 mg/L spectinomycin and 25 mg/L kanamycin and the cell density is adjusted to 0.2 at O.D.$_{660}$. The bacterium cell culture (50 mL in each 250-mL flask) is then put back on the shaker and grown overnight. On the morning of inoculation day, the bacterium cells are spun down and washed with liquid ½ MS VI medium (Table 1) supplemented with 200 µM of acetosyringone. After one more spinning, the bacterium cell pellet is re-suspended in ½ MS PL medium (Table 1) with 200 µM of acetosyringone (Table 1) and the cell density is adjusted to 1.0 at O.D$_{660}$ for inoculation.

Reagents are commercially available and can be purchased from a number of suppliers (see, for example Sigma Chemical Co., St. Louis, Mo.).

TABLE 1

Media used in this invention[1].

| Component | ½ MS VI | ½ MS PL | Co-culture medium | Induction MSW57 | MS/6BA | MSOD |
|---|---|---|---|---|---|---|
| MS salts | 68.5 g/l | 68.5 g/l | 2.2 g/l | 4.4 g/l | 4.4 g/l | 4.4 g/l |
| Sucrose | 20 g/l | 68.6 g/l | 20 g/l | 30 g/l | 30 g/l | — |
| Maltose | — | — | — | — | — | 20 g/l |
| Glucose | 10 g/l | 36 g/l | 10 g/l | — | — | 10 g/l |

TABLE 1-continued

Media used in this invention[1].

| Component | ½ MS VI | ½ MS PL | Co-culture medium | Induction MSW57 | MS/6BA | MSOD |
|---|---|---|---|---|---|---|
| 1-Proline | 115 mg/l | 115 mg/l | 115 mg/l | 1.36 g/l | 1.36 g/l | — |
| Casamino Acids | — | — | — | 500 mg/l | 50 mg/l | — |
| Glycine | 2 mg/l | 2 mg/l | 2 mg/l | 2 mg/l | — | — |
| 1-Asparagine | — | — | — | — | — | 150 mg/l |
| myo-Inositol | 100 mg/l | 100 mg/l | 100 mg/l | 100 mg/l | — | 100 mg/l |
| Nicotinic Acid | 0.5 mg/l | 0.5 mg/l | 0.5 mg/l | 0.5 mg/l | 1.3 mg/l | 1.3 mg/l |
| Pyridoxine•HCl | 0.5 mg/l | 0.5 mg/l | 0.5 mg/l | 0.5 mg/l | 0.25 mg/l | 0.25 mg/l |
| Thiamine•HCl | 0.1 mg/l | 0.1 mg/l | 0.6 mg/l | 0.6 mg/l | 0.25 mg/l | 0.25 mg/l |
| Ca Pantothenate | — | — | — | — | 0.25 mg/l | 0.25 mg/l |
| 2,4-D | — | — | 3 mg/l | 0.5 mg/l | — | — |
| Picloram | — | — | — | 2.2 mg/l | — | — |
| Silver Nitrate | — | — | 1.7 mg/l | 1.7 mg/l | — | — |
| BAP | — | — | — | — | 3.5 mg/l | — |

[1]Media ½ MSV I and ½ MSPL were used as liquid. Co-culture medium was solidified with 5.5 mg/l low EEO agarose. All other media were solidified with 7 g/l Phytagar for NPTII selection and with 3 g/l phytagel for glyphosate selection.

Example 3

Explant Preparation

Several genotypes of corn are used in this study. Ears containing immature embryos are harvested approximately 10 days after pollination and kept refrigerated at 4° C. until use (up to 5 days post-harvest). The preferred embryo size for this method of transformation is ~1.0-2.0 mm. This size is usually achieved 10 days after pollination inside the green house with the growth conditions of an average temperature of 87° F., day length of 14 hours with supplemental lighting supplied by GE 1 000 Watt High Pressure Sodium lamps.

Example 4

Inoculation

Immature embryos are isolated from surface sterilized ears and directly dropped into the prepared *Agrobacterium* cell suspension in 1.5-mL microcentrifuge tube. The isolation lasts continuously for 15 min. The tube is then set aside for 5 min, which results in an inoculation time for individual embryos of from 5 to 20 min. After the *Agrobacterium* cell suspension is removed using a fine-tipped sterile transfer pipette, the immature embryos are transferred onto the co-culture medium (Table 1). The embryos are placed on the medium with the scutellum side facing up. The embryos are cultured in a dark incubator (23° C.) for approximately 24 h.

Example 5

Selection, Regeneration and Growth of Transformants with Paromomycin Selection Immature embryos from a corn line are inoculated and co-cultivated with *Agrobacterium* as described above in Example 4. The embryos are then transferred onto a modified MS medium (MSW57, Table 1) supplemented with 100 or 200 mg/L paromomycin and 500 mg/L carbenicillin to inhibit *Agrobacterium* in Petri dishes (100 mm×25 mm). The cultures are incubated in a dark culture room at 27° C. for 2-3 weeks. All the callus pieces are then transferred individually onto the first regeneration medium (MS/6BA, Table 1) supplemented with the same levels of paromomycin. The cultures are grown on this medium and in a culture room with 16-h light/8-h dark photoperiod and 27° C. for 5-7 days. They are then transferred onto the second regeneration medium (MSOD, Table 1) in Petri dishes (100 mm×25 mm) for approximately 2 weeks. All the callus pieces with regenerating shoots and living tissue are transferred onto the same medium contained in phytatrays for shoots to grow further before being moved to soil. The regeneration media (MS6BA and MSOD) are all supplemented with 250 mg/L carbenicillin and 100 or 200 mg/L paromomycin.

Example 6

Selection, Regeneration and Growth of Transformants Through Glyphosate Selection Embryos inoculated and co-cultured with *Agrobacterium* are selected on the callus induction medium (MSW57, Table 1) supplemented with 0.1 or 0.25 mM glyphosate and 500 mg/L carbenicillin for approximately 3 weeks. All the callus pieces developed from individual embryos are regenerated the same way and under the same conditions as described in last section for the NPTII selection, except the MS6BA and MSOD media are supplemented with 250 mg/L carbenicillin and 0.1 or 0.25 mM glyphosate instead of paromomycin.

Example 7

Corn Callus Production

Corn seeds are kept in a desiccator for 2-24 h with sterilizing gas, which is produced by mixing of 200 mL bleach (5.25 to 6.15% sodium hypochlorite) and 2 mL HCl. (Seeds can also be sterilized in 50% bleach [bleach contains 5.25 to 6.15% sodium hypochlorite] for 20 min and washed with sterile water three times.) For germination, the kernels are inserted with the radicle end down into the medium. For germination, MSVS34 solid medium is used (MSVS34 medium is 4.4 g/L MS salts, 10 mL/L 100× MS vitamins, 40 g/L maltose, 100 mg/L casein, 1.95 g/L MES, 0.75 g/L magnesium chloride, and 0.5 g/L glutamine solidified with 7 g/L Phytagar with 3 mg/L BAP, 10 mg/L picloram and 100 mg/L ascorbic acid). Seeds are incubated in 16-hour day lighting at 28° C. for 7-10 days. On MSVS34 medium, the nodal area is expanded and no roots form at the nodal region. This area with apical and adventitious meristems usually produces the regenerable callus.

The nodal area (~0.5 cm long) of seedlings is isolated, cut longitudinally and placed with the wounded side down on MSW57 medium (Table 1). The cultures are incubated at 28° C. with a 16-h light photoperiod. After 3-4 weeks, calli are subcultured onto fresh medium and incubated in the dark at 28° C. Calli are subcultured onto fresh medium every 3-4 weeks until enough material is produced for transformation.

Example 8

Modulation of NO

This example describes the use of nitric oxide modulators in *Agrobacterium*-mediated transformation of corn. Corn callus and embryos, with and without previous inoculation in *Agrobacterium*, were cultured on medium containing NO donors (0.1 mM SNP and 0.01 mM SNAP), a NO-synthase inhibitor (1 mM L-NMMA), and the enantiomer of the inhibitor as negative control (1 mM D-NMMA, which has no effect on NO-synthase). All chemicals were obtained from EMD Biosciences, Inc. (La Jolla, Calif.). Callus and embryos, with and without previous inoculation in *Agrobacterium*, cultured on MSW57 (Table 1) were used as additional controls.

At Day 0, no significant differences in autofluorescence were detected for the different samples. Embryos stained with DAR-4M 4M, both non-inoculated and inoculated ones, showed a narrow region (strip) on both sides of the scutellum without NO, where GFP is generally preferentially observed.

At Day 3 and Day 6, autofluorescence increased over time, especially for explants treated with NO donors. Autofluorescence for explants treated with L-NMMA was dim compared to all other treatments and controls, with the exception of a biofilmlike material covering some areas of the explants at Day 3; however, when the explants were sectioned, no autofluorescence was observed on the cells from those areas.

The percentage of embryos and callus transformed was determined by observation under a dissecting scope equipped with U.V., whereas the number of events per explant was further confirmed following confocal observation. Callus sectioning was performed for image analysis at higher magnifications.

At Day 6, the percentage of embryos expressing GFP on medium with L-NMMA was 33% higher than the negative control (D-NMMA) and 8% higher than untreated controls. Also at Day 6, the percentage of callus expressing GFP was 50-52% higher than for controls, whereas the average number of events recorded per callus was 4.7 for untreated controls (61 in 13 callus), and 33 (132 in 4 callus) for callus treated with L-NMMA. Callus sectioning revealed that the number of transformed cells in L-NMMA-treated callus was higher than estimated.

The increase in the percentage of explants expressing GFP recorded on media with NO donors from Day 3 to Day 6 might be due to compound degradation. For embryos, cell proliferation of embryo-derived callus was significantly higher on medium containing SNAP, compared to other treatments and controls.

Confocal images confirmed this observation but showed significant differences in autofluorescent compounds accumulated in cells for the different treatments tested.

Limiting nitric oxide (NO) production in immature embryos and callus could increase transient GFP expression. In this experiment, there seemed to be a negative effect of the NO inhibitor N-monomethyl-L-arginine (L-NMMA) on callus induction from immature embryos.

To follow up on this callus induction observation, a new experiment was set up where a typical embryo harvest was done from several ears and the embryos were distributed onto control medium MSW57, MSW57 plus 1.0 mM L-NMMA or 0.1 mM S-nitroso-N-acetylpenicillamine (SNAP, a NO donor compound). In this experiment the embryos were placed on a dark Millipore filter set on top of two pieces of felt. The medium was liquid and a control on solid medium was added to determine if the liquid system had an adverse effect on callus induction. After 14-d in culture, it was apparent that continuous exposure to L-NMMA almost completely eliminated embryogenic callus induction. The callus exposed to the SNAP had more embryos with callus induction than the control, but the control response was so good that it was difficult to absolutely conclude that the SNAP treatment was better.

All publications patents, and patent applications mentioned in this specification are indicative of the level of skill of those skilled in the art to which this invention pertains. All publications, patents, and patent applications are herein incorporated by reference to the same extent as if each individual publication or patent application was specifically and individually indicated to be incorporated by reference.

Although the invention has been described in detail for the purpose of illustration, it is understood that such detail is solely for that purpose, and variations can be made therein by those skilled in the art without departing from the spirit and scope of the invention, which is defined by the following claims.

What is claimed is:

1. A method of transforming a plant cell or plant tissue using an *Agrobacterium*-mediated process comprising the steps of:

inoculating a transformable plant cell or tissue with *Agrobacterium* containing at least one genetic component capable of being transferred to said transformable plant cell or tissue;

culturing said transformable plant cell or tissue on at least one plant transformation medium comprising an effective amount of at least one nitric oxide modulator, said culturing resulting in a transformed plant cell or tissue; and regenerating a transformed plant expressing said genetic component from said transformed plant cells or tissue.

2. The method of claim 1 wherein said at least one nitric oxide modulator is selected from the group comprising $N^G$-monomethyl-L-arginine, monoacetate salt ($N^G$-Me-L-Arg, AcOH; L-NMMA); $N^G$-monomethyl-L-homoarginine, monoacetate salt (NMMHA, AcOH); $N^G$-monoethyl-L-arginine, monoacetate salt (NMEA, AcOH); $N^G$-monomethyl-L-arginine, di-p-hydroxyazobenzene-p''-sulfonate salt ($N^G$-Me-L-Arg,diHABS; L-NMMA); and clinorotation.

3. The method of claim 2 wherein said at least one nitric oxide modulator is at least one nitric oxide inhibitor.

4. The method of claim 3 wherein said at least one nitric oxide inhibitor is L-NMMA.

5. The method of claim 4 wherein the amount of L-NMMA is between about 5 µM and about 100 µM.

6. A method of producing a transformed corn plant comprising inoculating a transformable corn cell or tissue with *Agrobacterium* containing at least one genetic component capable of being transferred to said transformable plant cell or tissue;

culturing said transformable corn cell or tissue on a co-culture transformation medium comprising an effective amount of at least one nitric oxide modulator, said culturing resulting in a transformed corn cell or tissue; and regenerating a transformed corn plant expressing said genetic component from said transformed corn cells or tissue.

7. The method of claim 6 in which said at least one nitric oxide modulator is at least one nitric oxide inhibitor.

8. The method of claim 6 in which said at least one nitric oxide inhibitor is L-NMMA.

9. The method of claim 8 in which the amount of L-NMMA is about 10 μM.

10. A method of treating a plant cell during an *Agrobacterium* transformation process with at least one nitric oxide modulator.

* * * * *